United States Patent [19]

Lowicki et al.

[11] 4,454,153

[45] Jun. 12, 1984

[54] ZINC SALT OF A HYDROLYZED TRICARBOXYLIC ACID FROM ENE-ADDUCTS OF MALEIC ANHYDRIDE TO UNDECYLENIC ACID

[75] Inventors: Norbert Lowicki, Duisburg; Natvarlal B. Desai, Dinslaken, both of Fed. Rep. of Germany

[73] Assignee: Grillo-Werke Aktiengesellschaft, Duisburg-Hamborn, Fed. Rep. of Germany

[21] Appl. No.: 400,394

[22] Filed: Jul. 21, 1982

Related U.S. Application Data

[63] Continuation-in-part of Ser. No. 240,606, Mar. 4, 1981, Pat. No. 4,376,789.

[30] Foreign Application Priority Data

Jul. 29, 1981 [DE] Fed. Rep. of Germany ....... 3129826

[51] Int. Cl.$^3$ .................... A61K 31/315; C09F 5/00
[52] U.S. Cl. ................. 424/289; 260/404.8; 424/DIG. 4
[58] Field of Search ................. 260/404.8; 424/289, 424/DIG. 4

[56] References Cited

U.S. PATENT DOCUMENTS

| | | | |
|---|---|---|---|
| 2,569,420 | 9/1951 | Kosmin | 260/404.8 |
| 3,420,859 | 1/1969 | Ueno et al. | 424/289 X |
| 4,150,041 | 4/1979 | Suzuki et al. | 260/404.8 X |
| 4,307,089 | 12/1981 | Melloh | 260/404.8 X |
| 4,374,852 | 2/1983 | Hilditch et al. | 424/289 |
| 4,379,753 | 4/1983 | Bolich | 424/289 |

FOREIGN PATENT DOCUMENTS

| | | |
|---|---|---|
| 0023676 | 2/1981 | European Pat. Off. . |
| 0046970 | 3/1982 | European Pat. Off. . |
| 2460205 | 8/1975 | Fed. Rep. of Germany . |
| 2125219 | 9/1972 | France . |

*Primary Examiner*—Natalie Trousof
*Assistant Examiner*—Vera C. Clarke
*Attorney, Agent, or Firm*—Marshall, O'Toole, Gerstein, Murray & Bicknell

[57] ABSTRACT

The zinc salt of the hydrolyzed tricarboxylic acid from Diels-Alder adducts or ene-adducts of maleic anhydride to undecylenic acid, preferably in a molar ratio of from 0.8 to 1.2, are described as skin-compatible bactericides and fungicides. They are preferably used in cosmetic preparations. They are more active and less toxic than the substances previously known and used for said purposes.

13 Claims, No Drawings

ZINC SALT OF A HYDROLYZED TRICARBOXYLIC ACID FROM ENE-ADDUCTS OF MALEIC ANHYDRIDE TO UNDECYLENIC ACID

This application is a continuation-in-part of our co-pending U.S. patent application Ser. No. 240,606 filed Mar. 4, 1981, now U.S. Pat. No. 4,376,789.

The present invention relates to zinc salts of a hydrolyzed tricarboxylic acid from ene-adducts of maleic anhydride to undecylenic acid, a process of preparing same, and the use thereof as skin-compatible bactericides and fungicides, more particularly in cosmetic preparations.

Ene-adducts or Diels-Alder adducts, respectively, of maleic anhydride with at least mono unsaturated carboxylic acids are known. They may be saponified with an alkali, and their esters and amides, particularly their reaction products with triethanolamine, have been known as anticorrosive agents; cf. U.S. Pat. No. 3,985,504.

The alkali salts of said acids have also been used to prevent the formation of precipitates from hot sea water; cf. British Pat. No. 1,551,894. The chemical structure of the adducts apparently was not completely determined for a long period of time, since the respective teachings in the two aforementioned patents are contradictory. According to U.S. Pat. No. 3,985,504, the addition takes place at the carbon atoms adjacent to the double bond, while the double bond itself is retained. According to British Pat. No. 1,551,894, cyclobutane dicarboxylic acids are formed. In any event, tri- and polyvalent carboxylic acids result from the hydrolysis of the adducts.

In the meantime it has been established that maleic anhydride forms adducts with mono unsaturated carboxylic acids, in which adducts one carbon atom of the double bond of maleic anhydride and one carbon atom of the double bond of the unsaturated carboxylic acid are attached to each other so as to form a new carbon to carbon single bond, while the second carbon atom of the maleic anhydride double bond is converted to an active $CH_2$ group. The double bond of the carboxylic acid is retained, but it is shifted to the next carbon atom located closer to the carboxylic group. According to the more recent nomenclature, this reaction is called an "ene reaction", and the respective adducts are now named "ene-adducts". Said reaction was first described in the year 1962 in Liebig's Annalen der Chemie 651, p. 141.

It has already been proposed to prepare partial esters of di- and higher polyhydric alcohols, more specifically also of mono- and disaccharides, with the Diels-Alder adducts or ene-adducts, respectively, of at least mono unsaturated carboxylic acids having a chain length of from $C_{10}$ to $C_{25}$ so as to obtain and use skin-compatible nonionic surfactants. The optionally sulfonated partial esters of the undecylenic acid have been mentioned to be useful as skin-compatible, mildly bactericidal and fungicidal, nonionic and/or anionic surfactants in cosmetic preparations as disclosed in our parent U.S. patent application Ser. No. 240,606 filed Mar. 4, 1981, now U.S. Pat. No. 4,376,789 the entire content of which is incorporated herein by reference.

It has now been found according to the invention that the zinc salts of the hydrolyzed tricarboxylic acids from ene-adducts of maleic anhydride to undecylenic acid exhibit surprisingly high bactericidal and fungicidal activity while not being irritating to the skin and yet very compatible. Therefore, they are very suitable for use in toiletries where biocidal activity which spares the skin is especially desired as, for example, in agents for personal hygiene and pedicure and for use in shampoos for dandruff.

The zinc salts of the hydrolyzed tricarboxylic acids from ene-adducts of maleic anhydride to undecylenic acid according the present invention are considerably superior, with respect to their efficacy and compatibility, to all previously known substances used for said purposes. Moreover, said properties render the substances suitable for use as preservatives in cosmetic preparations, as no physiologically detrimental effects are thereby caused or expected.

The zinc salts according to the invention contain certain amounts of free carboxylic acid groups, depending on the conditions of preparation. Thus, the molar ratio of zinc to tricarboxylic acid generally ranges from 0.8 to 1.2; however, zinc salts having a higher or lower zinc content may also be prepared and used according to the invention.

The preparation of the zinc salts is most readily accomplished by hydrolyzing the ene-adducts of maleic anhydride to undecylenic acid with an aqueous alkali solution and subsequently reacting the product of the hydrolysis with a water-soluble zinc salt. The reaction may basically be carried out in a temperature range of about 0° C. to 100° C.; however, temperatures between about 50° C. to 80° C. are preferred.

The zinc salt is added to the acid in about an equimolar amount, preferably in an amount in the range from 0.9 to 1.3 mol per 1 mol of tricarboxylic acid. As a matter of course, higher or lower amounts of zinc salt may also be employed to produce the zinc salt according to the invention having a higher or lower content of zinc. Using the aforementioned process conditions yields a zinc salt precipitate which contains about 1 mol of zinc per 1 mol of tricarboxylic acid and has a pH of 5.5 to 5.7.

Even though the antimicrobial activities of the salts of undecylenic acid, more particularly of the zinc salt, has been known, these salts have only found limited use in hair cosmetics. Said salts, which are also incorporated in compositions widely used as anti-dandruff agents in hair cosmetics (including selenium disulfide, zinc pyrithione), because of their high solubility and/or their limited activity on hair and the skin of the head, respectively, restricts their action to the actual process and time of washing the hair.

The surprisingly high efficacy of the zinc compound according to the present invention, which has a higher anti-microbial or fungicidal in vitro activity comared to the known compounds, appears to a large extent to be due to the presence of a free carboxylic acid group which significantly increases the activity of the zinc compound of the invention towards hair and skin of the head. Another beneficial feature of said carboxylic acid group is the fact that the zinc compounds of the invention give a slightly acidic reaction, thereby denaturing the biosphere of the skin of the head for fungi, more specifically of the Pythirosporum type.

The anti-dandruff activity of the zinc compound according to the invention is distinctly superior to that of, for example, zinc pyrithione, and this is apparently so because the novel zinc compound is stronger and influences hair and the skin of the head for an extended period of time in the desired way.

The present invention is further illustrated by way of the following examples which illustrate the preparation of the zinc salt of the tricarboxylic acid and toiletry products containing the same.

EXAMPLE 1

184.2 g of undecylenic acid (1 mol) is reacted with 98 g of maleic anhydride (1 mol) without solvent while stirring in a three-necked flask under a nitrogen atmosphere at 170° C. to 175° C. for 5 hours. Upon completion of the reaction, the reaction product is cooled down to 60° C. to 70° C. and then hydrolyzed with aqueous NaOH to yield the hydrolyzed tricarboxylic acid from ene-adducts of maleic anhydride to undecylenic acid. 287.46 g of $ZnSO_4.7H_2O$ dissolved in 1000 ml of water is subsequently added at 70° C. The precipitated zinc salt of the tricarboxylic acid is washed several times with distilled water and then dried at 70° C. The yield is 290 g. The product was analyzed and found to have a zinc content of 17.52%. The theoretical value calculated on the basis of a 1:1 molar ratio is 17.97% zinc.

EXAMPLE 2

Anti-Dandruff Shampoo

| | |
|---|---|
| Zinc salt according to Example 1 | 2.0% |
| Sodium lauryl ether sulfate (28%) | 34.0% |
| Coconut fatty acid diethanolamide | 2.5% |
| Sodium chloride | 2.0% |
| Water | 59.5% |
| | 100.0% |

EXAMPLE 3

Personal Hygiene Washing Solution

| | |
|---|---|
| Zinc salt according to Example 1 | 0.5% |
| Sulfonated partial ester of ethylene glycol of the Diels-Alder adduct of maleic anhydride with undecylenic acid (Compound A - prepared as per below) | 10.0% |
| Ricinoleic acid monoethanolamide sulfosuccinate | 15.0% |
| Sodium laurylether sulfate (28%) | 20.0% |
| Comperlan KD (Coconut fatty acid diethanolamide - Henkel KGaA, Germany) | 3.0% |
| Polyglycol 400 | 10.0% |
| Polyol fatty acid ester | 7.0% |
| Water | 34.5% |
| | 100.0% |

PREPARATION OF COMPOUND A 184.3 g of undecylenic acid (1 mol) is reacted with 98 g of maleic anhydride (1 mol) without a solvent and without a catalyst, with agitation under a nitrogen atmosphere at 170°–175° C. for five hours. After termination of the reaction, the reaction product is cooled to 60°–70° C. and water is added. The polycarboxylic acid is then esterified in the same reaction vessel with ethylene glycol at 130°–135° C. This yields a partial ester of ethylene glycol with an acid number of about 100.

The partial ester is sulfonated with 252 g of sodium sulfite heptahydrate dissolved in 300 g of water at 80° C. in one hour to yield a clear, light-brown strongly foaming solution.

EXAMPLE 4

Foot Powder—Antimycotic

| | |
|---|---|
| Talc | 72.0% |
| China clay | 20.0% |
| Rice starch | 5.2% |
| Zinc salt according to Example 1 | 2.5% |
| Aerosil 2000 (Pyrogenic silicon dioxide) | 0.3% |
| | 100.0% |

EXAMPLE 5

Personal Hygiene Deodorant Lotion

| | |
|---|---|
| Grillocin Hy 77 (Deo-agent based on zinc ricinoleate - Grillo AG, Germany) | 1.0% |
| Cremophor (Fatty alcohol polyglycolether) | 1.0% |
| Mono- and diglycerides of palmitic and stearic acids | 6.0% |
| Triglyceride of saturated fatty acids | 4.0% |
| Paraffin oil | 6.0% |
| Cetyl alcohol | 1.0% |
| 1,2-Propyleneglycol | 3.0% |
| Zinc salt according to Example 1 | 0.3% |
| Water | 77.7% |
| | 100.0% |

The high antimicrobial activity of the salt according to Example 1 was tested. The results are listed in the following Table 1. The minimal inhibitory concentrations (MIC) are shown in Table 2.

The acute toxicity of the salt according to Example 1 was tested with rats. The oral $LD_{50}$ was found to be in excess of 16,000 mg/kg for male as well as female rats. According to N. P. Lupke and P. Preusser, Antischuppenkosmetika—Wirkung and Toxikologie (Anti-Dandruff Cosmetics—Effects and Toxicology), Arztliche Kosmetologie 8, p. 5, 1978, the toxicities of anti-dandruff agents so far used, expressed in terms of $LD_{50}$ values for rats, range between 56 and 1,120. The individual values were as follows:

| | | |
|---|---|---|
| Hexachlorophene | males | 66 |
| | females | 56 |
| Selenium disulfide | | 138 |
| Zinc pyrithione | males | 200 |
| | females | 140 |
| Sodium pyrithione | males | 1,120 |
| | females | 980 |

Thus, the substance according to the present invention is far less toxic than the prior art substances.

In order to determine the dermal compatibility of the zinc compound according to the invention, a test was conducted on intact and scarified skin of rabbits. The test was carried out in a way similar to that according to the conditions of the U.S. Consumer Product Safety Commission (Code of Federal Regulations, Title 16, Section 1500.41). The evaluation of the skin reaction was made in accordance with the ETAD recommendations. Neither erythemae nor oedemae were observed on the intact as well as on the scarified skin after 24 hours, and 72 hours, respectively.

Examination of the subchronic and chronic toxicity for rats using doses of 15, 375, and 939 ppm contained in the food resulted in no negative effects in the course of 3 months, whereas at comparable doses of zinc 2-pyridinethiol-1-oxide there were observed many cases of palsy of the rear extremities and death. An undiluted shampoo according to Example 2 causes only a slight irritation of the rabbit eye, whereas upon application of a shampoo containing zinc 2-pyridinethiol-1-oxide all of the tested animals were observed to suffer from cornea damage.

TABLE 1

Antimicrobial Activity of the Compound According to Example 1

Concentration: 2%

| Time of Reaction min. | Escherichia coli | Staphylococcus aureus | Trichophyton mentagrophytes | Candida albicans | Pityrosporon ovale |
|---|---|---|---|---|---|
| 2.5 | − | − | − | − | − |
| 5.0 | − | − | − | − | − |
| 10.0 | − | − | − | − | − |
| 20.0 | − | − | − | − | − |
| 30.0 | − | − | − | − | − |
| Blank Test* | +++ | +++ | + | ++ | + |
| Starting Germ Content per ml of Inoculated Solution | 280,000 | 120,000 | 24,000 | 9,000 | 440,000 |

*Growth: +++ very strong;
++ significant;
+ weak;
− none.

TABLE 2

Values of the Minimal Inhibitory Concentration (MIC) of the Compound of Example 1

| MIC Determined by Dilution Test | Escherichia coli | Staphylococcus aureus | Pseudomonas aeruginosa | Candida albicans | Pityrosporon ovale |
|---|---|---|---|---|---|
| Cocn. (%) of the original substance* | | | | | |
| 10% | − | − | − | − | − |
| 5% | − | − | − | − | − |
| 2.5% | − | − | − | − | − |
| 1.0% | − | − | − | − | − |
| 0.5% | − | − | − | − | − |
| 0.1% | − | (+) | (+) | − | − |
| 0.05 | (+) | + | + | (+) | (+) |
| Number of Test Germs | 82,000 | 26,000 | 73,000 | 4,000 | 8,500 |

*Growth: − none;
(+) sporadic;
+ significant.

What is claimed is:

1. A zinc salt of a hydrolyzed tricarboxylic acid from ene-adducts of maleic anhydride to undecylenic acid.

2. A zinc salt according to claim 1, characterized in that the molar ratio of zinc is from 0.8 to 1.2 mol per mol of tricarboxylic acid.

3. A toiletry product having bactericidal and fungicidal activity containing about 0.3 to 2.5% by weight of a zinc salt of a hydrolyzed tricarboxylic acid from ene-adducts of maleic anhydride to undecylenic acid and a toiletry product carrier.

4. A toiletry product according to claim 3 in the form of a cosmetic preparation.

5. A toiletry product according to claim 3 in the form of a shampoo.

6. A toiletry product according to claim 3 in the form of a foot powder.

7. A toiletry product according to claim 3 in the form of a lotion.

8. A toiletry product according to claim 3 in which the carrier includes water.

9. A toiletry product according to claim 3 in which the carrier includes talc.

10. A toiletry product having bactericidal and fungicidal activity comprising a carrier and an effective amount of a zinc salt according to claim 1.

11. A method of effecting bactericidal and fungicidal activity on hair and/or skin which comprises applying a safe and effective amount of a zinc salt of a hydrolyzed tricarboxylic acid from ene-adducts of maleic anhydride to undecylenic acid, to the hair and/or skin.

12. A method according to claim 11 in which the zinc salt is applied to the hair and/or skin in the form of a toiletry product containing about 0.3 to 2.5% by weight of the zinc salt and a toiletry product carrier.

13. A method according to claim 12 in which the toiletry product is a shampoo, foot powder or lotion.

* * * * *